United States Patent [19]

Girardot

[11] Patent Number: 4,976,733
[45] Date of Patent: Dec. 11, 1990

[54] PREVENTION OF PROSTHESIS CALCIFICATION

[75] Inventor: Jean-Marie Girardot, Dunwoody, Ga.

[73] Assignee: Biomedical Design, Inc., Atlanta, Ga.

[21] Appl. No.: 303,577

[22] Filed: Jan. 27, 1989

Related U.S. Application Data

[63] Continuation-in-part of Ser. No. 151,653, Feb. 3, 1988, abandoned.

[51] Int. Cl.$^5$ .......... A61F 2/02; A61F 2/06; A61F 2/22; A61F 2/24
[52] U.S. Cl. .......... 623/11; 623/1; 623/2; 623/3; 623/66; 523/113; 427/2; 427/417; 8/94.11; 8/94.20
[58] Field of Search .......... 623/1, 2, 3, 11, 66, 623/12; 523/112, 113; 524/308; 525/454; 514/60; 427/2, 417; 8/94.11, 94.20, 94.22, 94.23

[56] References Cited

U.S. PATENT DOCUMENTS

| | | | |
|---|---|---|---|
| 4,553,974 | 11/1985 | Dewanjee | 623/1 X |
| 4,831,065 | 5/1989 | Pietsch et al. | 524/308 X |

*Primary Examiner*—Alan W. Cannon
*Attorney, Agent, or Firm*—Fitch, Even, Tabin & Flannery

[57] ABSTRACT

A method for retarding or preventing the calcification of a prosthesis implanted in a mammal by covalently coupling to the prosthesis before implantation an effective amount of an anticalcification agent in the form of an aliphatic carboxylic acid, or a derivative thereof, which contains from about 8 to about 30 carbon atoms and which may be straight-chain or branched-chain and saturated or unsaturated. Such acid is substituted by at least one amino, mercapto, carboxyl or hydroxyl group by which the covalent coupling takes place. For a natural tissue prosthesis, such coupling may be to an aldehyde group of gluteraldehyde in which the tissue is pre-soaked.

11 Claims, No Drawings

PREVENTION OF PROSTHESIS CALCIFICATION

This application is a continuation-in-part of my earlier application, Ser. No. 151,653, filed Feb. 3, 1988, now abandoned.

The present invention relates to a method for retarding or preventing the calcification of a prosthesis implanted in a mammal such as a human.

BACKGROUND OF THE INVENTION

The surgical implantation of prosthetic devices (prostheses) into humans and other mammals has been carried out in recent years with increasing frequency. Such prostheses include, by way of illustration only, heart valves, vascular grafts, urinary bladders, heart bladders, left ventricular-assist devices, hip prostheses, silastic breast implants, tendon prostheses, and the like. They may be constructed from natural tissues, inorganic materials, synthetic polymers, or combinations thereof. By way of illustration, mechanical heart valve prostheses typically are composed of rigid materials, such as polymers, carbons, and metals, and employ a poppet occluder which responds passively with changes in intracardiac pressure or flow. Valvular bioprostheses, on the other hand, typically are fabricated from either porcine aortic valves or bovine pericardium; in either case, the tissue is pretreated with glutaraldehyde and then sewn onto a flexible metallic alloy or polymeric stent which subsequently is covered with a poly(ethylene terephthalate) cloth sewing ring covering. The assembled prostheses (often referred to in the literature as bioprostheses) are stored in 0.2 percent glutaraldehyde. Examples of reference of a more general nature include Helen E. Kambic et al., "Biomaterials In Artificial Organs," *Chem. Eng. News*, Apr. 14, 1986, pp. 31–48; and Frederick J. Schoen, "Pathology of Cardiac Valve Replacement," Chapter 8 in D. Morse et al., Editors, "Guide to Prosthetic Cardiac Valves," Springer-Verlag, N.Y., 1985, pp. 209–238.

Prostheses derived from natural tissues are preferred over mechanical devices because of certain significant clinical advantages. Tissue-derived prostheses generally do not require routine anticoagulation. Moreover, when they fail, they usually exhibit a gradual deterioration which can extend over a period of months, or even years. Mechanical devices, on the other hand, typically undergo catastrophic failure.

While any prosthetic device can fail because of mineralization, and especially calcification, this cause of prosthesis degeneration is especially significant for tissue-derived prostheses. Indeed, calcification has been stated to account for over 60 percent of the failures of cardiac bioprosthetic valve implants. Despite the clinical importance of the problem, the pathogenesis of calcification is incompletely understood. Moreover, there apparently is no effective therapy known at the present time.

References which discuss the calcification problem and its prevention include. among others. R. J. Levy et al., "Bioprosthetic Heart Valve Calcification: Clinical Features, Pathobiology, and Prospect for Prevention," *CRC Review in Biocompatibility*, 2, 147–187 (1986); Frederick J. Schoen et al., "Calcification of Bovine Pericardium Used in Cardiac Valve Bioprostheses," *Am. J. Pathol.*, 123, 134–145 (1986); Robert J. Levy et al., "Inhibition by Diphosphonate Compounds of Calcification of Porcine Bioprosthetic Heart Valve Cusps Implanted Subcutaneously in Rats," *Circulation*, 71, 349–356 (1985); Gershon Golomb et al., "Inhibition of Bioprosthetic Heart Valve Calcification by Sustained Local Delivery of Ca and Na Diphosphonate via Controlled Release Matrices," *Trans. Am. Soc. Artif. Intern. Organs*, 32, 587–590 (1986); R. J. Levy et al., "Local Controlled-Release of Diphosphonates from Ethylenevinyllacetate Matrices Prevents Bioprosthetic Heart Valve Calcification" *Trans. Am. Soc. Artif. Intern. Organs*, 31, 459–463 (1985); and Frederick J. Schoen et al., "Onset and Progression of Experimental Bioprosthetic Heart Valve Calcification," *Lab. Invest.*, 52, 523–532 (1985).

As a reading of many of the foregoing references will show, previous efforts at preventing the calcification of tissue-derived prostheses include:

(a) detergent pretreatment of the prosthesis;

(b) daily injection of a diphosphonate, such as 1-hydroxyethylidene diphosphonic acid;

(c) covalent binding of a diphosphonate, such as 1-hydroxy-3-aminopropane-1,1-diphosphonic acid, to bioprosthetic tissue proteins via residual aldehyde groups remaining after a glutaraldehyde pretreatment; and (d) controlled-release, site-specific diphosphonate delivery by an osmotic pump or a controlled-release matrix, such as an ethylene-vinyl acetate copolymer, typically with 1-hydroxyethylidene diphosphonic acid or 1-hydroxy-3-aminopropane-1,1-diphosphonic acid as the diphosphonate. Suitable polymers typically include those disclosed in U.S. Pat. No. 4,378,224 to Moses J. Folkman et al.; see, also, U.S. Pat, Nos. 4,164,560 and 4,391,797, both to Moses J. Folkman and Robert S. Langer, Jr., neither of which appears to be directed to preventing calcification. For a similar disclosure which also does not appear to be directed at preventing calcification of implanted prostheses, see U.S. Pat. No. 4,357,312 to Dean S. T. Hsieh and Robert S. Langer, Jr. In addition to the two diphosphonates mentioned [see, also, Krammsch et al., *Circ. Res.*, 42, 562–571, (1978)], other anticalcification agents which apparently are suitable for controlled-release applications include calcium channel blockers such as nifedipine [Henry et al., *J. Clin. Invest.*, 68. 1366-1369 (1981)]; calcium chelating agents such as ethylenediamine-tetraacetic acid [Wartman et al., *J. Atheroscler, Res.*, 7, 331–341 (1967)]; ionic antagonists such as lanthanum trichloride [Kramsch, supra]; thiophene compounds [Krammsch, supra]; and phosphocitrate analogues such as 2-aminotricarballylate.

As a variation of method (c), above, pretreatments of fixed natural tissue prostheses which apparently do not involve covalent binding are known. Several representative references are described below.

U.S. Pat. No. 4,402,697 to Elisabeth M. Pollock and David J. Lent describes a pretreatment using a solution of a water-soluble phosphate ester such as sodium dodecyl hydrogen phosphate.

A similar pretreatment using a solution of a water-soluble quaternary ammonium salt such as dodecyltrimethylammonium chloride is described in U.S. Pat, No. 4,405,327 to Elisabeth M. Pollock.

Finally, U.S. Pat. No. 4,323,358 to David J. Lentz and Elisabeth M. Pollock describes a pretreatment using a solution of a water-soluble salt of a sulfated higher aliphatic alcohol, such as sodium dodecyl sulfate.

While such methods were capable of lowering bioprosthetic tissue calcification, they are not free from difficulties. For example, detergent pretreatment, while having a short-term effectiveness, does not appear to be a viable approach for the long-term inhibition of tissue calcification. Diphosphonate injection at effective levels is accompanied by severe untoward effects on bone and overall somatic growth. The use of an osmotic pump requires the subdermal surgical implantation of the pump, and the long-term supply of the anticalcification agent administered by the pump is an issue which must be addressed. The long-term administration of an anticalcification agent also is an issue with controlled-release methods. In addition, the glutaraldehyde pretreatment used with all cardiac bioprostheses apparently facilitates prosthesis tissue calcification.

Thus, there is a pressing need for a more effective method for reducing or preventing the calcification of prostheses.

SUMMARY OF THE INVENTION

Accordingly, the present invention provides a method for retarding or preventing the calcification of a prosthesis implanted in a mammal by covalently coupling to the prosthesis before implantation an effective amount of an anticalcification agent in the form of a substituted aliphatic carboxylic acid or a derivative thereof. The acid contains from about 8 to about 30 carbon atoms, and it may be straight-chain or branched-chain and saturated or unsaturated. The covalent coupling is via the substituent moiety which may be an amino, a mercapto, a carboxyl or a hydroxyl group. Also, the invention provides prostheses suitable for implantation in a mammal made by the aforesaid method.

In one preferred embodiment, the anticalcification agent is a substituted aliphatic carboxylic acid which contains from about 12 to about 24 carbon atoms and no more than about three carbon-carbon double bonds. In a particularly preferred embodiment, the anticalcification agent is a substituted aliphatic straight-chain carboxylic acid which contains from about 12 to about 22 carbon atoms and one carbon-carbon double bond.

The method of the present invention is useful for retarding or preventing the calcification of a prosthesis implanted in a mammal, such as a human, and has particular application with respect to those prostheses which are especially susceptible to degeneration as a result of calcification.

DETAILED DESCRIPTION OF THE INVENTION

As used herein, the term "prosthesis" is meant to include any device which is implanted in a mammal. Thus, the term includes heart valves and other heart components, vascular replacements or grafts, artificial hearts, urinary tract and bladder replacements, bowel and tissue resections in general, left ventricular-assist devices, hip replacements, silastic breast implants, artificial tendons, electrodes, catheters, and the like. However, it will be recognized by those having ordinary skill in this art that the present invention may be of most importance in relation to prostheses for which calcification after implantation has been a clinical problem. Thus, while the present invention can be used with essentially any prosthesis, it may not be as beneficial for a prosthesis which is not likely to suffer degeneration or malfunction as a result of mineralization.

The material from which the prosthesis is prepared is not critical. Thus, the prosthesis can be one which is made from natural tissues, including but not limited to bovine, ovine, porcine, and human tissue; metals; synthetic organic materials, such as polyurethanes, polyetherurethanes; silicones; polyesters; polycarbonates; polyacrylates and methacrylates; polyacetates; polyolefins, such as polyethylene and polypropylene; polyalcohols; combinations and derivatives thereof; and the like. Other materials, well known to those having ordinary skill in the art, also can be used.

In general, the anticalcification agent is selected from the group consisting of aliphatic carboxylic acids and alkali metal salts and derivatives thereof, each of which acids can contain from about 8 to about 30 carbon atoms. Preferably, the anticalcification agent will contain from about 12 to about 22 or 24 carbon atoms and most preferably from about 15 to about 20 carbon atoms. The preferred alkali metal salts are the potassium and sodium salts.

The anticalcification agent may be a straight-chain or a branched-chain compound which is appropriately substituted. Except for the substituent through which covalent linking is achieved, the nature and number of the substituents are not critical, provided that they do not significantly adversely effect the anticalcification properties of the compound and also that such substituents do not have a significant adverse physiological effect upon implantation of the prosthesis treated with such agent. In general, the number and nature of substituents present should be such that a very rigid molecule is avoided. Examples of substituents which can be present include alkyl, alkenyl, alkynyl, cycloalkyl, cycloalkenyl, cycloalkynyl, aryl, hydroxy, alkoxy aryloxy, carbonyl, halo, amino, alkylamino, dialkylamino, arylamino, diarylamino, alkylarylamino, mercapto, alkylthio, arylthio, and the like. As explained in more detail hereinafter, there should be at least one substituent selected from amino, hydroxy, mercapto and carboxyl to create the desired covalent linkage.

The acids which comprise the anticalcification agents of the present invention can be saturated or unsaturated. Such unsaturation can be monounsaturation or polyunsaturation resulting from the presence in the compound of one or more ethylenic or acetylenic groups, i.e., one or more carbon-carbon double bonds, one or more carbon-carbon triple bonds, or a combination of one or more carbon-carbon double bonds and one or more carbon-carbon triple bonds. Moreover, such double or triple bonds can be present anywhere in the molecule. In addition, carbon-nitrogen double and/or triple bonds also can be present, provided such bonds do not adversely affect either the anticalcification properties or physiological compatibility of the compound. Carbon-carbon double bonds are the preferred unsaturation, with one or two of such bonds being more preferred. Most preferably, the anticalcification agent will have a single carbon-carbon double bond in the main carboxylic acid chain, independent of the presence or absence of unsaturation in any substituents which may be present.

It may be noted at this point that the present invention contemplates the use of a single anticalcification agent as well as a mixture of two or more different anticalcification agents. If a mixture is employed, such mixture may include a free acid and a salt thereof, or more than one free acid or salts of different acids, as well as derivatives of any of the foregoing. Thus, the use of the term "anticalcification agent" throughout this specification and the appended claims is meant to include a single anticalcification agent and any mixture of two or more anticalcification agents, including such mixtures as those set forth above.

As used herein, the term "derivative" is meant to include any compound having at least one portion or moiety which is substantially an aliphatic carboxylic acid as defined hereinabove. By way of clarification, such aliphatic carboxylic acid may be represented by the general formula,

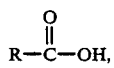

with R representing the aliphatic chain with the carboxyl group preferably located at one end thereof. For a moiety to consist substantially of such aliphatic carboxylic acid, it should contain at least the portion,

the aliphatic carboxylic acid. Preferably, such moiety will contain the portion,

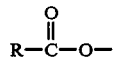

of the aliphatic carboxylic acid. As will become evident later, if a derivative is employed, it should still be covalently coupled to the prosthesis through the aliphatic carboxylic acid portion of the molecule, lest the aliphatic carboxylic acid portion be removed from the prosthesis as a result of hydrolysis or other reaction of the derivative.

As a practical matter, derivatives of the aliphatic carboxylic acids which comprise the anticalcification agents of the present invention typically will be either esters or amides, with esters being preferred. By way of illustration, examples of suitable classes of esters are given below.

(1) aliphatic, cycloaliphatic, and aromatic esters of the aliphatic carboxylic acids;

(2) phosphoric acid esters of the aliphatic carboxylic acids; and (3) mono- and polyesters of one or more aliphatic carboxylic acids, which may be the same or different, with di- or polyhydric aliphatic or aromatic alcohols, optionally via a phosphoric acid ester group, examples of such mono- and polyesters including, by way of illustration only, 1- monoacylglycerols, 2-monoacylglycerols, 1,2-diacylglycerols, triacylglycerols, alkyl ether acylglycerols, glycosyldiacyl-glycerols, phosphoglycerides, plasmalogens, sphingolipids, waxes, and the like.

Examples of aliphatic carboxylic acids coming within the foregoing definition include, among others, octanoic acid, 2-aminooctanoic acid, oct-3-enoic acid, 2-methyl-nonanoic acid, 10-hydroxydec-5-ynoic acid, undecanoic acid, phenyltetradecanoic, 3-chloro-8-(2-hydroxylethoxy)pentadec-4-en-9-ynoic acid, hexadecanoic acid, hexadec-9-enoic acid, 3,7-dimethylhexadec-9-enoic acid, octadec-9-enoic acid (oleic acid), 2-aminooctadec-9-enoic acid, octadec-9,12-dienoic acid, octadec-9,12,15-trienoic acid, eicosanoic acid, eicos-5,8,11,14-tetraenoic acid, tetracosanoic acid, and the like. These would be used in suitably substituted form, such as 2-aminooctanoic acid, 10-hydroxydec-5-ynoic acid, 12-amino dodecanoic acid, 2-aminooctadec-9-enoic acid (2-amino oleic acid) and 2,2-dicarboxyl octadec-9-enoic acid.

As already noted, included within the definition of anticalcification agents are the alkali metal salts of the aliphatic carboxylic acids. Also included are esters of such acids with monohydric alcohols, as well as mono- and polyesters with polyhydric alcohols, examples of which alcohols include, by way of illustration only, methanol, ethanol, 2-(4-ethoxyphenyl)ethanol, 2-chloropropanol, 1-butanol, 2-butanol, hex-3-en-1-ol, octanol, eicosanol, phenol, 3-methylphenol, 1,2-ethanediol, 1,4-butanediol, glycerol, L-glycerol 3-phosphoric acid, phosphoric acid, sphingosine, dihydrosphingosine, cholesterol, lanosterol, cholic acid, aldosterone, esterone, testosterone, and the like.

As already noted, the method of the present invention involves covalently coupling an anticalcification agent to a prosthesis. As a consequence of such covalent coupling, the anticalcification agent will certainly be associated with the surfaces of the prosthesis. However, such agent also may migrate into, and become associated with, part or all of the bulk materials from which the prosthesis is constructed, depending upon a number of factors such as the porosity of the materials and the permeability of such materials to the anticalcification agent. For the purposes of this invention, no distinction is made between the location of the agent on the surfaces only or with partial or complete penetration into the bulk materials. That is, the term "covalent coupling" and variations thereof include the coupling of the anticalcification agent to the prosthesis surfaces only and also coupling of the anticalcification agent to part or all of the bulk materials of which the prosthesis is composed.

Reaction conditions for the covalent coupling of the anticalcification agent to the prosthesis may vary, depending upon the presence or absence of biomaterials, the type of functional groups present on the prosthesis, the nature of the anticalcification agent, and the coupling chemistry to be employed. In general, the coupling reaction typically will be carried out in an aqueous solution which may be buffered at a suitable pH. The nature of the buffer is not believed to be critical. Examples of suitable buffers include phosphate, tartrate, bicarbonate, borate, citrate, formate, acetate, N-2-hydroxyethylpiperazine-N'-ethanesulfonic acid (HEPES), tris(hydroxymethyl) aminomethane (TRIS), 3-(N-morpholino)propanesulfonic acid (MOPS), and the like. For additional details on buffers, see, e.g., Gerald D. Fasman, Editor, "CRC Handbook of Biochemistry and Molecular Biology," 3rd Edition, Physical and Chemical Data Volume I, CRC Press, Inc., Boca Raton, Fla., 1976, pp.354–377. In addition, the buffer concentration is not critical and can vary widely. The pH of the buffer also can vary over a wide range, typically from about 6 to about 14. Thus, the pH of the buffer preferably will be in the range of from about 7 to 11, most preferably from about 9 to about 11, and in such a buffer the carboxylic acid anticalcification agent will usually be in the form of its alkali metal salt, e.g., the sodium salt.

The concentration of the anticalcification agent in the aqueous solution can vary, for example, from about 0.1 percent by weight or less to about 20 percent by weight or more. As a practical matter, less concentrated solutions are preferred, with concentrations in the range of from about 0.1 percent to about 5 percent perhaps being typical.

The coupling reaction may be carried out at any temperature which does not adversely affect the prosthesis, e.g., from about 0° C. to about 100° C., unless the prosthesis is composed in whole or in part of biomaterials, i.e., tissue, in which case the temperature typically will not exceed about 40° C. As a practical matter, however, such aqueous solution will be at ambient temperature. Exposure time can vary over a wide range, e.g., from about 5 minutes to about a week, and it will be dependent upon the particular coupling reaction being utilized and the overall conditions. In general, very long exposure times, e.g., more than a week, do not appear to be necessary. Thus, the exposure time may be in the range of from about 10 minutes to about 24 hours; however, for tissue materials, as opposed to synthetic polymeric materials, coupling reactions may be carried out at room temperature for periods of about five days or even longer to assure that an adequate amount of the agent is covalently bonded to the prosthesis.

After a sufficient reaction time (incubation), the prosthesis is rinsed or washed to remove excess reaction solution. The rinse or wash solution can be distilled water, deionized water, a buffer, or any other suitable liquid. If the prosthesis contains biomaterial, it is not allowed to dry; such biomaterial prosthesis is preferably stored in, for example, 0.2 percent, buffered aqueous glutaraldehyde solution.

By way of illustration only, when 2-aminooleic acid or a salt thereof is to be covalently coupled to a bioprosthesis, the treating solution typically will be a buffer, such as borate buffer, having a pH in the range of from about 8 to about 11. Incubation can vary from about 2 hours or less to about 24 hours or more, and incubation periods of from about 48 hours to about 120 hours are preferred for tissue prostheses. While the incubation temperature can range from about 0° C. to about 40° C., temperatures from about 20° C. to about 35° C. appear to be preferred.

In general, covalent coupling of the anticalcification agent to a prosthesis may be accomplished by any of a variety of methods known to those having ordinary skill in the art. Such methods typically involve such reactive substituent groups as amino, carboxy, hydroxy, and mercapto. Representative coupling methods involve, by way of illustration only, carboxylic acid azide groups, carboxylic acid chlorides, carbodiimides and Woodward's reagent, diazotization, isothiocyanates, cyanuric chloride, cyanogen bromide, titanium chloride activation, the Ugi reaction, the use of intermediate coupling agents, such as organofunctional silanes, peptide bond formation, the formation of a Schiff's base, as well as the formation of an ester linkage between a carboxyl group substituent and a free hydroxy group on the prosthesis, to name but a few. See, e.g., Howard H. Weetall, "Immobilization by Covalent Attachment and by Entrapment," Chapter 6 in Ralph A. Messing, Editor, "Immobilized Enzymes for Industrial Reactors," Academic Press, New York, 1975, pp. 99-123; and William H. Scouten, Editor, "Solid Phase Biochemistry. Analytical and Synthetic Aspects," John Wiley & Sons, Inc., New York, 1983. Moreover, further chemical modification can be accomplished after coupling the anticalcification agent to the prosthesis. For example, the carbon-nitrogen double bond of the Schiff's base can be reduced, e.g., by reaction with sodium borohydride under mild conditions, to increase the stability of the coupled material, e.g., against hydrolysis. It will be appreciated by those having ordinary skill in the art, however, that not all coupling methods necessarily can be used with any given prosthesis. That is, the coupling chemistry to be employed is in part dependent upon the nature of the functional groups present on the prosthesis.

The present invention is further described by examples which follow. Such examples however, are not to be construed as limiting in any way either the spirit or the scope of the present invention. In the examples, all percentages are percents by weight and all temperatures are in degrees Celsius, unless otherwise specified.

EXAMPLE 1

The method of the present invention is illustrated by the covalent coupling of an amino-substituted oleic acid anticalcification agent to bovine pericardium tissue.

I. Formation of Oleic Acid Agent

A substituted oleic acid compound is synthesized in a form which is well suited for covalently coupling to glutaraldehyde-treated bovine pericardium tissue or other natural tissue by a linkage which takes advantage of the glutaraldehyde pretreatment of the tissue. To prepare the compound, 2-aminooleic acid, the procedure of F. Amat Guerri, *Grasas Aceites (Seville)*, 26. 90 (1975), was generally followed. The series of reactions described below was repeated three times, with similar results, in order to accumulate a supply of intermediates and the final compound. Only one reaction sequence is described, however.

A. Preparation of 2-(Hexadec-7-enyl)propane Dicarboxylic Acid

A 250-ml., three-necked, round-bottomed flask was fitted with a 50ml. pressure-equalized side arm addition funnel, condenser, and rubber septum. The addition funnel and condenser also were fitted with rubber septa. The flask was purged continuously with dry nitrogen (Matheson extra dry grade) which was introduced via a syringe needle inserted through the rubber septum fitted on one of the three necks of the flask; the nitrogen exited via another syringe needle inserted through the condenser-mounted rubber septum. Using a syringe, the flask was charged with 21.5 ml. (0.155 mole) of diisopropylamine (99 percent, Aldrich chemical Company, Inc., Milwaukee, Wis.) and 50 ml. of dry tetrahydrofuran (THF) (Gold Label, 99.9 percent, Aldrich Chemical Company, Inc.). The resulting solution was cooled in an ice-salt bath while being stirred with a magnetic stirrer. To the cold solution (of the order of −20 to −10 degrees) was added slowly 60 ml. of n-butyllithium in hexane (Aldrich Chemical Company, Inc.) which had been added via a syringe to the addition funnel. The resulting mixture was stirred for two hours, after which time 20.0 g. (0.071 mole) of oleic acid (Fisher Scientific, Pittsburgh, Pa.) was added dropwise by means of the addition funnel (charged by syringe injection), over a one-hour period; during the addition, the reaction solution turned dark red, indicating the formation of the dianion. To the reaction mixture then was added dropwise over an approximately 30-minute period a mixture of 51 g. of hexamethylphosphoramide (Aldrich Chemical Company, Inc., 99 percent, which has been dried over calcium hydride and then stored over a molecular sieve) and 50 ml. of THF, the two liquids having been added previously to the addition funnel by syringe injection. The resulting mixture was stirred for one hour and poured into a 600ml. beaker containing 100 g. of solid carbon dioxide (the red color disappeared immediately upon contacting the dry ice). The mixture was allowed to stir overnight. The reaction mixture, now a pale yellow solution at ambient temperature, was acidified with approximately 40 ml. of concentrated hydrochloric acid, an amount sufficient to turn blue litmus paper red. The acidified solution was extracted three times with 100-ml. portions of diethyl ether (Fisher Scientific). The ether extracts were combined, washed once with distilled water, and dried over anhydrous magnesium sulfate (reagent grade, J. T. Baker Chemical Co.). The ether solution was decanted from the drying agent and evaporated under reduced pressure by means of a rotating evaporator (Buchi Rotovap, Model RE 120). The residue was a pale yellow semisolid weighing 20.2 g. (87 percent yield).

B. Preparation of Diethyl 2-(Hexadec-7-enyl) Propane Dicarboxylate

A solution of 5 g. (15.3 mmole) of the product from step A, above, four drops of concentrated hydrochloric acid as catalyst, and 100 ml. of 95 percent ethanol (Mallinckrodt, Inc., St. Louis, Mo.) was heated at reflux temperature for two hours in a 250-ml. single-necked round-bottomed flask fitted with a condenser. The solvent was removed by distillation at atmospheric pressure. The light yellow residue then was distilled at about 0.1 mm Hg to yield 5.1 g. (87 percent) of a clear, colorless oil, b.p. 140-3 at 0.1 mm Hg, which was shown to be diethyl 2-(hexadec-7-enyl) propanedicarboxylic acid by infrared analysis (absorption maxima were observed at 1735, 1710, and 1190 cm$^{-1}$).

C. Preparation of Ethyl 2-Hydroxyiminooctadec-9-eneoate

The method of D. J. Drinkwater and P. W. G. Smith, *J. Chem. Soc.*, 1971, 1305, was followed. A 50-ml., three-necked, round-bottomed flask was fitted with a pressure-equalized addition funnel and charged with 1.0 g. (2.62 mmole) of diethyl 2-(hexadec-7-enyl) propanedicarboxylate. The material was cooled to about −10 degrees while being stirred magnetically. The flask then was charged with 0.27 g. (2.62 mmole) of n-butylnitrite (Aldrich Chemical Company, Inc.), followed by the addition over a period of one hour of a sodium ethoxide solution prepared by reacting 0.06 g. of sodium spheres (Aldrich Chemical Company, Inc.) with 1.8 ml. of absolute ethanol. The reaction mixture then was stirred overnight at −10 degrees. Ethanol was removed under reduced pressure and the residue was mixed with an equal volume of ice water. The resulting solution was washed with diethyl ether and the pH was adjusted to 5 by the addition of hydrochloric acid while being cooled in an ice bath. The acidified solution was extracted twice with 50-ml. portions of diethyl ether. The ether extracts were combined, dried over anhydrous magnesium sulfate, and decanted from the drying agent. The ether was removed under reduced pressure to give 0.79 g. (85 percent) of the desired product as shown by infrared analysis (absorption maxima were observed at 3260 and 1734 cm$^{-1}$).

D. Preparation of 2-Hydroxyiminooctadec-9-enoic Acid

A mixture of 0.6 g. (1.77 mmole) of ethyl 2-hydroxyiminooctadec-9-eneoate and 20 ml. of 1 N aqueous sodium hydroxide was heated at reflux temperature for 10 minutes. The reaction mixture was cooled, acidified with concentrated hydrochloric acid, and extracted twice with 50-ml. portions of diethyl ether. The extracts were combined, dried over anhydrous magnesium sulfate, and decanted from the drying agent. The ether was removed to give a light yellow oil which was recrystallized from ether-light petroleum (b.p. 40–60 degrees, Fisher Scientific) to yield 0.5 g. (91 percent) of 2-hydroxyiminooctadec-9-eneoic acid. Infrared analysis of the material showed absorption maxima at 3220, 3080, and 1695 cm$^{-1}$.

E. Preparation of 2-Aminooleic Acid

A mixture of 0.7 g. of 2-hydroxyiminooctadec-9-enoic acid, 0.77 g. of zinc powder (Fluka Chemical Corporation, Ronkonkoma, N.Y.), and 12.3 ml. of a 2:1 glacial acetic acid: water mixture was heated at reflux temperature for 90 minutes. The reaction mixture was filtered through a fine scintered glass funnel while still hot, and the filtrate was allowed to cool overnight in a freezer. A solid had precipitated which was filtered on a Buchner funnel to yield 0.61 g. (91 percent) of white, powdery 2-aminooleic acid, m.p. 216-7 degrees (dec.). The material was analyzed by infrared spectroscopy in a potassium bromide pellet; absorption maxima were seen at 3200–3500 and 1650 cm$^{-1}$.

II. Covalent Coupling of 2-Aminooleic Acid to Bovine Pericardium Cusps

2-Aminooleic acid, as the sodium salt, was coupled to two groups of ten glutaraldehyde-pretreated bovine pericardium cusps (the cusps were obtained from a local slaughterhouse and stored in 0.2 percent aqueous glutaraldehyde solution) by simply incubating the cusps overnight at ambient temperature in a 1.0 percent solution of the anticalcification agent in 0.05 M sodium borate buffer at pH 11. Coupling occurred through residual aldehyde groups via Schiff base formation. After incubation, the cusps were rinsed ten times with 10-ml. portions of physiological saline solution (0.9 percent aqueous sodium chloride).

Each group of foregoing treated cusps was implanted subcutaneously in the ventral mid-abdominal area of a group of five three-week old Sprague-Dawley rats (Charles River Breeding Laboratories, Inc., Wilmington, Mass.), two cusps per rat (one on each side). The implantation procedure was essentially the same as that described in U.S. Pat, No. 4,402,697. One group of ten untreated cusps was implanted as a first control. As a second control, a group of ten cusps was incubated in 0.05 M, pH 11 sodium borate buffer which did not contain an anticalcification agent.

Two separate studies were conducted. After 21 days, the implanted cusps were removed from the rats and analyzed for calcium by atomic absorption spectrometry as described by Frederick J. Schoen et al., *Am. J. Pathol.* 123, 134–145 (1986), supra. The animals were sacrificed and autopsied; no abnormalities were observed. A group of ten untreated cusps which had not been implanted also was analyzed for calcium. The results are summarized in Table 1.

TABLE 1

Effect of Covalent Coupling of 2-Aminooleic Acid
on the Calcification of Bovine Pericardium Cusps
Implanted Subcutaneously in Rats

| Group | Tissue Ca Concentration |
| --- | --- |
| Untreated, unimplanted | 2.3 ± 0.5 |
| Implanted, untreated | 142.6 ± 6.8 |
| Implanted, untreated[a] | 141.7 ± 12.8 |
| Implanted, treated | 1.5 ± 0.2 |
| Implanted, untreated[a] | 144.0 ± 7.9 |
| Implanted, treated | 0.8 ± 0.4 |

[a]Incubated overnight at ambient temperature in 0.05 M, pH 11 HEPES buffer.

The effectiveness of the covalently coupled 2-aminooleic acid in inhibiting mineralization is readily apparent from Table 1. Calcium concentrations in the treated tissues were at levels equivalent, or perhaps even lower, than the level of calcium normally present in the tissue.

The significance of the method of the present invention is made more evident upon studying the effect of a generally similar, but non-covalently linked, anticalcification agent on the calcification process. Such a study is detailed in Examples 2 and 3.

EXAMPLE 2

Several process variables were studied with regard to pretreatment of tissue prostheses before carrying out implantation experiments with respect to a non-covalently bound anticalcification agent.

Incubation Time

Glutaraldehyde-treated bovine pericardium cusps were incubated at ambient temperature in 1 percent by weight aqueous solution of sodium oleate which contained $^{14}C$-labeled sodium oleate for one and seven days, respectively. The solution pH was 10.6. The cusps were washed ten times with 10-ml. portions of 0.05 M HEPES buffer at pH 7.4. The cusps then were analyzed for sodium oleate uptake. The results are summarized in Table 2.

TABLE 2

Sodium Oleate Concentration in Tissue
after One and Seven Days

| Incubation Period | Tissue NaOleate Concn. |
| --- | --- |
| One day | 119.3 nmoles/mg. tissue |
| Seven days | 124.2 nmoles/mg. tissue |

The data in Table 2 show essentially no difference in tissue uptake of sodium oleate, indicating that incubation times of longer than one day, with non-covalently bound sodium oleate, do not appear to substantially increase uptake.

Effect of Wash pH

The above described procedure was repeated, using a concentration of sodium oleate of 10 percent instead of 1 percent and an incubation period of one day. Three groups of cusps were employed. One group of cusps were not washed; they were blotted to remove excess fluid. The second group was washed with distilled water, and the third group was washed with pH 7.4 HEPES buffer as described above. Table 3 summarizes the results.

TABLE 3

Sodium Oleate Concentration in Tissue
under Varying Wash Conditions

| Wash Medium | Tissue Na Oleate Concn. |
| --- | --- |
| None (blotted) | 845.2 nmoles/mg. tissue |
| Distilled water | 263.9 nmoles/mg. tissue |
| Buffer, pH 7.4 | 631.9 nmoles/mg. tissue |

It may be noted that the buffer wash resulted in a lower amount of sodium oleate being removed from the tissue as a consequence of the washing step. In addition, it appears that the use of a 10 percent sodium oleate significantly increases tissue pickup of sodium oleate, compared with a 1 percent sodium oleate solution.

In order to evaluate the effect of an extended wash cycle, the above experiment was repeated. At the end of the incubation period, cusps were immersed in 10 cc of either distilled water or pH 7.4 HEPES buffer. The cusps were agitated on a shaking platform at 37 degrees for 16 days. The cusps then were analyzed for tissue sodium oleate. The results are summarized in Table 4.

TABLE 4

Sodium Oleate Concentration in Tissue
under Varying Wash Conditions

| Wash Condition | Tissue NaOleate Concn. |
| --- | --- |
| Distilled water | 15.5 nmoles/mg. tissue |
| Buffer, pH 7.4 | 218.2 nmoles/mg. tissue |

The data in Table 4 again demonstrate the advantages to a pH 7.4 wash compared with a distilled water wash.

EXAMPLE 3

Two groups, each containing ten glutaraldehyde-treated bovine pericardium cusps per group, were incubated for two hours at ambient temperature in solutions containing 1 percent sodium oleate (Fisher Scientific). The first solution was obtained by dissolving the sodium oleate in 0.05 M, pH 7.4 HEPES buffer. The second solution was obtained by dissolving the sodium oleate in distilled water; the solution pH was 10.6.

Each group of cusps was implanted subcutaneously in rats as described in Example 1. Two control groups of the same size also were established by cusps which had not been pretreated with sodium oleate.

The first control group of rats received daily sterile saline injections subcutaneously, one injection of 500 microliters per animal per day. The saline was 0.9 percent aqueous sodium chloride solution having a pH of 7.4. The second control group received equivalent daily injections of a sodium oleate solution at a level of 100 mg. sodium oleate per kg. of body weight per 24-hour period.

After 14 days, the cusps were retrieved from all four groups. The animals were sacrificed and autopsied, with the sodium oleate-injected animals showing lower blood calcium levels. The cusps were analyzed for calcium by atomic absorption spectrometry as described in Example 1. The results are summarized in Table 5.

TABLE 5

Effect of Sodium Oleate Treatment
on the Calcification of Bovine Pericardium Cusps
Implanted Subcutaneously in Rats

| Group | Tissue Ca Concentration[a] |
| --- | --- |
| 1st Control (saline injection) | 70.4 ± 12.8 |
| 2nd Control (Na oleate injection) | 62.3 ± 8.3 |

TABLE 5-continued

Effect of Sodium Oleate Treatment
on the Calcification of Bovine Pericardium Cusps
Implanted Subcutaneously in Rats

| Group | Tissue Ca Concentration[a] |
|---|---|
| Na Oleate pretreatment, pH 7.4 | 51.4 ± 6.2 |
| Na Oleate pretreatment, pH 10.6 | 34.7 ± 7.9 |

[a]Reported as the mean of micrograms calcium per mg. of cusp tissue ± standard error.

The data in the above table show that pretreatment of a prosthesis with sodium oleate reduces calcification. While the reduction in calcification was of the order of 30 to 50 percent, based on the first control, such reduction is not believed to be sufficient for the long-term retardation or prevention of calcification. It is likely that the sodium oleate is associated with the prosthesis tissue only on the basis of hydrogen bonding and Van der Waals forces. Such association may be readily disrupted with the probability that the sodium oleate is removed from the locus of the implant, thus rendering it less effective than a covalently coupled anticalcification agent.

EXAMPLE 4

Treatment of Glutaraldehyde-Preserved Porcine Tissue With 2-Amino Oleic Acid Sodium Salt (2-AOASS) and With 12-Amino Dodecanoic Acid Sodium Salt (12-ADASS)

The cusps or leaflets from glutaraldehyde-preserved porcine valves were dissected, rinsed for 5 min. with sterile physiological saline (0.9% NaCl, 10 cusps in 50 ml.) and placed in 10 mM sodium borate, pH 11.0. This allows the excess glutaraldehyde to be washed out of the tissue and also to adjust the pH of the leaflets.

The cusps were placed in 1% (w/v) solution (1 cusp per b 2 ml.) of either 2-AOASS or 12-ADASS and incubated without shaking for the varying times and at the varying temperatures indicated in Experiments A-D hereinafter. The control leaflets were incubated under similar conditions but in the absence of active anticalcification agents. After incubation, the cusps were rinsed twice with 50 ml. of 10 mM sodium borate buffer, pH 11.0, to remove unbound material and twice with 50 ml. of distilled water. The cusps were then stored in 0.2% buffered glutaraldehyde solution. It is possible that some of the anticalcification agent that permeates into the tissue during incubation but associates with it without being covalently bonded may become cross-linked therewithin during storage in the 0.2% glutaraldehyde solution and add to anticalcification protection. Experiments to date have not proved that cross-linking in fact occurs. Immediately prior to implantation, the cusps were rinsed with sterile physiological saline to remove the excess glutaraldehyde.

One control and one or two treated cusps were implanted subcutaneously in three-week old male rats (30 to 50 g.) as set forth with regard to Example 1.

After 21, 60, 90 or 120 days the implants were retrieved, cleaned of adherent tissue and rinsed 5 times with sterile physiological solution and 5 times with distilled water. The explanted tissue was lyophilized, weighted and hydrolyzed in an oxygen-free atmosphere in 6 N HCl for 24 hr. at 110° C. The hydrolysates were dried and resolubilized in dilute HCl, and the calcium level was determined by the Inductively Coupled Plasma Analysis method.

Experiment A

The treated samples were glutaraldehyde-preserved cusps incubated at room temperature (about 22° C.) for 24 hours with either 2-AOASS or 12-ADASS at a concentration of 1% (w/v). The control samples were glutaraldehyde-preserved cusps incubated in the absence of active agents. Both treated and control cusps were implanted for 21, 60, 90 and 120 days. The results are presented in Table A below:

TABLE A

| Implant time (days) | Ca++ µg./mg. dry tissue Mean ± SEM | | | |
|---|---|---|---|---|
|  | n | Control | n | Treated |
| 2-AOASS | | | | |
| 21 | 2 | 169.5 ± 12.3 | 3 | 56.8 ± 42.5 |
| 60 | 10 | 318.6 ± 20.0 | 10 | 200.4 ± 26.8 |
| 90 | 10 | 235.5 ± 6.5 | 11 | 120.7 ± 26.1 |
| 120 | 10 | 279.6 ± 6.7 | 11 | 181.1 ± 32.5 |
| 12-ADASS | | | | |
| 21 | 3 | 170.0 ± 3.5 | 3 | 119.1 ± 32.2 |
| 60 | 10 | 283.6 ± 17.7 | 10 | 213.7 ± 18.1 |
| 90 | 6 | 227.5 ± 6.8 | 6 | 217.7 ± 7.0 |
| 120 | 6 | 286.1 ± 8.0 | 6 | 250.0 ± 23.3 |

The above results indicate that treatment of porcine cusps for 24 hours at room temperature with 2-AOASS partially prevents calcification of implants while treatment for a similar period with 12-ADASS has a lesser effect.

Experiment B

The glutaraldehyde-preserved cusps were incubated for 48 hours at 33° C. in either buffer alone (control), buffer containing 2-AOASS (1% w/v) or buffer containing 12-ADASS (1% w/v) and implanted for 21 days. The data are presented in Table B:

TABLE B

| Implant time 21 days | Ca++ µg./mg. dry tissue Mean ± SEM | | | |
|---|---|---|---|---|
|  | n | Control | n | Treated |
| 2-AOASS | 5 | 123.9 ± 11.1 | 5 | 2.1 ± 0.7 |
| 12-ADASS | 5 | 112.8 ± 8.6 | 5 | 10.1 ± 7.7 |

The above results demonstrate that treatment for 48 hours with either 2-AOASS or 12-ADASS strongly prevents calcification of leaflets during 21 days of subcutaneous implantation in rats.

Experiment C

The glutaraldehyde-preserved cusps were treated for 48 hours at 33° C. in either buffer (controls) or in buffer containing 2-AOASS (1% w/v) and were implanted for 21, 60, 90, or 120 days in three-week old rats. The data are presented in Table C:

TABLE C

| Implant time (days) | Ca++ µg./mg. dry tissue Mean ± SEM | | | |
|---|---|---|---|---|
|  | n | Control | n | Treated |
| 21 | 5 | 145.6 ± 12.0 | 8 | 2.8 ± 1.1 |
| 60 | 2 | 231.5 ± 2.2 | 4 | 25.7 ± 24.1 |
| 90 | 2 | 279.2 ± 20.9 | 4 | 77.0 ± 48.0 |
| 120 | 2 | 243.5 ± 9.5 | 4 | 5.0 ± 1.8 |

The data reported in Table C show that calcification of glutaraldehyde-preserved porcine cusps is inhibited after 48 hours incubation in the presence of a 1% (w/v)

suspension of 2-amino oleic acid sodium salt. The lack of complete inhibition in the 60 and 90 day-implants could be attributed to differences in thickness of certain of the cusps. The diffusion of the active agent through the porcine tissue (i.e., collagen bundles) may be rate-limiting because other experiments showed that for thinner natural tissue materials, particularly bovine pericardium tissue, shorter incubation times result in adequate absorption of an anticalcification agent of this type. Complete inhibition is seen in the samples implanted for 21 and for 120 days.

Experiment D

Three rats were implanted with one control, one 24 hour- and one 120 hour-2-AOASS-treated cusps. The temperature of incubation was 22° C., and the concentration of 2-AOASS was 1% (w/v). After 60, 90, or 120 days the leaflets were retrieved and analyzed for calcium content. The results are presented in Table D:

TABLE D

| Implant time | Ca++ μg. dry/mg. tissue | | |
|---|---|---|---|
| | | Treated | |
| (days) | Control | 24 h | 120 h |
| 60 | 271.5 | 126.8 | 1.9 |
| 90 | 232.9 | 149.2 | 2.0 |
| 120 | 298.6 | 229.0 | 2.9 |

The data presented demonstrate that 2-AOASS treatment for 120 hours completely prevents calcification of glutaraldehyde-preserved porcine leaflets for up to 120 days of implantation in three-week old rats, whereas incubation for 24 hours, although not nearly as good, is significantly effective.

EXAMPLE 5

Binding studies, generally similar to those carried out in Example 2 with respect to sodium oleate, are performed with 2-amino oleic acid by employing tritium-labeled 2-amino oleic acid having a specific activity of about 23 cpm/nanomole. The radioactive anticalcification agent is suspended at three different concentrations, namely, 0.1%, 0.5% and 1% weight/volume in a sodium borate buffer at 10 millimolar concentrations and a pH of 11.0. Glutaraldehyde-preserved cusps are incubated in the solution of 33° C. for 24, 48 and 96 hours. The incubated cusps are rinsed in the binding buffer and in distilled water to remove the unbound anticalcification agent. Half of each cusp is used for a retention study while the other half was lyophilized, weighted as dry tissue and then measured for radioactivity by a liquid scintillation counter. As expected, in each instance, maximum uptake of the compound was obtained as a result of incubation in the 1% solution for each specific time period of incubation; a greater uptake of the compound was obtained after 24 hours in a 1% solution than for 96 hours in a 0.1% solution.

The specific results are set forth in Table E.

TABLE E

| Binding of 2-Amino Oleic Acid to Glutaraldehyde-Preserved Porcine Cusps | | | |
|---|---|---|---|
| AOASS Solution | Incubation Time | | |
| (w/v) % | 24 hr. | 48 hr. | 96 hr. |
| 0.1% | 5* | 13 | 27 |
| 0.5% | 15 | 19 | 35 |
| 1.0% | 27 | 30 | 38 |

*amounts are reported as nanomoles of AOASS per mg. of dry tissue.

The remaining halves of the cusps are used for the retention study and are immersed in a pH 7.4 phosphate buffer for 2 months at 22° C. and then lyophilized, weighed and similarly measured for radioactivity. The results show the same general relationship to one another as reported in Table E with all retaining a major portion, usually more than 75% of the bound AOASS. The samples that were incubated in the 1% solution, however, showed the greatest retention of the anticalcification agent with retentions of more than 80% for incubation of 48 hours or more. In general, samples incubated for 96 hours retained a greater percent of AOASS than those incubated for lesser periods of time. Based upon all the foregoing studies it is generally felt that generally porous material prostheses, such as those formed of natural tissue, should include at least about 15 nanomoles of anticalcification agent per milligram of dry tissue and preferably at least about 30 nanomoles. The surface portions of prostheses made from relatively impervious synthetic materials should have equivalent amounts attached thereto.

Although the foregoing studies have been directed to the treatment of natural tissue materials where calcification is a significant problem with respect to prostheses presently being implanted, primarily in humans, as earlier indicated, the invention is considered to be also applicable to preventing the calcification of prostheses made from synthetic polymeric material, which material either naturally incorporates potentially chemically active groups through which covalent binding can be achieved or which can be appropriately modified so as to incorporate such groups. For example, some of the most commonly employed materials for prostheses are the polyurethanes, and synthetic materials in the form of either polyester or polyether polyurethanes can be treated in this manner. Examples of these includes those sold under the trademarks Biomer by Athicon, Inc., Lycra, T-127 by DuPont, Pellethane CPR 2363 by Upjohn, and Texin by Mobay Chemical Corp., which polymers are composed of 4,4'-diisocyanatodiphenyl methane (MDI) and a polyol such as polytetramethylene ether glycol (PTMEG). Another that is commonly employed is Cardiothane which is a polyurethane-polydimethylsiloxane (90%-10%) copolymer marketed by Kontron, Inc.

These polymers are composed of hard and soft segments, and after implantation, the calcification of segmented polyurethanes occurs primarily in the soft segments. Therefore, binding or attachment of anticalcification agents, such as 2-amino oleic acid, 12-amino dodecanoic acid or analogues and derivatives, is most appropriately directed toward soft segments, although binding to hard segments is also possible. For instance, the following two approaches are considered feasible for providing urethane polymers with such anticalcification protection by means of the incorporation of an appropriately substituted aliphatic carboxylic acid. The synthetic polymer may be formed with certain grafts that will serve as binding sites and thereafter treated with the anticalcification agent, even after the prostheses has been physically formed; alternatively, an initial reaction can be carried out between the anticalcification agent and a diol that will later serve as one of the reactants in the formation of the polyurethane when the final polymerization step is thereafter carried out.

With respect to the formation of polymers with suitable graft sites, a diol could be used having functional groups such as aldehydes, carboxyls or blocked isocyanates. Two such diols having carboxyl functionality are 2,2-bis hydroxy methyl propionic acid and N,N-bis hydroxy ethyl glycine. If employed in such a reaction, the resulting prepolymers could have either of the following structures:

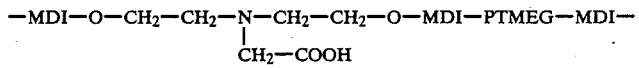

or

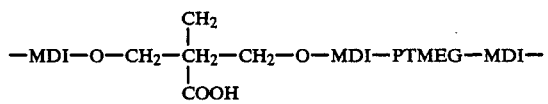

Such polymer chain can then be extended using a short diol, such as 1,4 butanediol. After such chain elongation, an anticalcification agent containing an amino constituent could be attached via the grafted carboxyl groups using a carbodiimide to form the peptide bond. Alternatively, the anticalcification agent could be reacted with the prepolymer before the chain elongation reaction with the BDO. Very generally, suitable polyurethanes could be formed employing reactants in the following approximate ratios for each three moles of MDI: between about 1.3 and 2 moles of PTMEG, between about 0.9 and 1 mole of BDO, and the remainder being the graft-containing diol. Using the general conditions outlined above, the anticalcification agent will be located mainly in the soft segments of the polymer, although some might be near the hard segment.

Still another example of inclusion of an anticalcification agent in a urethane polymer prosthesis would be to form a higher molecular weight PTMEG containing a suitable graft site by reacting PTMEG 1000 with

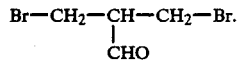

Such a higher molecular weight PTMEG containing the free aldehyde grafts should react normally in the polyurethane formation, and thereafter the free aldehyde groups will serve as covalent bonding sites for suitable amino-substituted or mercapto-substituted aliphatic carboxylic acids or derivatives thereof.

Having thus described the invention with particular reference to either illustrative or preferred embodiments, it will be obvious to those having ordinary skill in the art to which the invention pertains that numerous variations and changes can be made without departing from the spirit and scope of the invention as defined by the appended claims. Particular features of the invention are emphasized in the claims that follow.

What is claimed is:

1. A prosthesis suitable for implantation in a mammal, which prosthesis has an amount of an anticalcification agent covalently coupled thereto sufficient to retard or prohibit the calcification of the prosthesis, which anticalcification agent comprises an aliphatic straight-chain or branched-chain, saturated or unsaturated, carboxylic acid or a derivative thereof, which acid contains from about 8 to about 30 carbon atoms, and which acid is substituted with an amino group, a mercapto group, a carboxyl group or a hydroxyl group, which group is covalently coupled to said prosthesis.

2. The prosthesis of claim 1, in which said anticalcification agent is a monocarboxylic acid or derivative thereof.

3. The prosthesis of claim 2, in which said monocarboxylic acid is monosaturated with ethylenic unsaturation.

4. The prosthesis of claim 4, in which said substituent is an amino group.

5. The prosthesis of claim 4, in which said monocarboxylic acid is a straight-chain monocarboxylic acid.

6. The prosthesis of claim 5, in which said monocarboxylic acid is oleic acid or dodecanoic acid.

7. The prosthesis of claim 5, in which said acid is 2-amino oleic acid.

8. The prosthesis of claim 4 wherein said prosthesis is a tissue prosthesis and wherein said covalent linking to said prosthesis is via connection to an aldehyde group of glutaraldehyde which is in turn linked to said tissue prosthesis.

9. The prosthesis of claim 1, in which said anticalcification agent is an acid which contains from about 12 to about 24 carbon atoms and no more than about three carbon-carbon double bonds.

10. The prosthesis of claim 1, in which said anticalcification agent is a straight-chain acid which contains from about 12 to about 22 carbon atoms and only one carbon-carbon double bond.

11. The prosthesis of claim 10 wherein said substituent is attached to the carbon atom adjacent to the carboxylic acid group.

* * * * *